United States Patent
Ohtsuki et al.

(10) Patent No.: US 9,724,662 B2
(45) Date of Patent: Aug. 8, 2017

(54) EXHAUST GAS MIXER AND CONSTANT VOLUME SAMPLING APPARATUS

(71) Applicant: HORIBA, Ltd., Kyoto (JP)

(72) Inventors: Satoshi Ohtsuki, Kyoto (JP); Tatsuki Kumagai, Kyoto (JP); Sayaka Yoshimura, Kyoto (JP); Yoshiko Tsuji, Kyoto (JP)

(73) Assignee: Horiba, Ltd., Kyoto (JP)

( * ) Notice: Subject to any disclaimer, the term of this patent is extended or adjusted under 35 U.S.C. 154(b) by 92 days.

(21) Appl. No.: 14/228,462

(22) Filed: Mar. 28, 2014

(65) Prior Publication Data
US 2014/0293732 A1 Oct. 2, 2014

(30) Foreign Application Priority Data
Mar. 29, 2013 (JP) ................................. 2013-074767

(51) Int. Cl.
*B01F 15/00* (2006.01)
*B01F 15/02* (2006.01)
(Continued)

(52) U.S. Cl.
CPC .... *B01F 15/0227* (2013.01); *B01F 15/00123* (2013.01); *G01N 1/2252* (2013.01); *G01N 15/06* (2013.01); *G01N 2001/2255* (2013.01)

(58) Field of Classification Search
CPC ... G01N 1/2252; B01F 5/0057; B01F 5/0071; B01F 5/0074; B01F 2005/0017;
(Continued)

(56) References Cited

U.S. PATENT DOCUMENTS 3,953,184 A * 4/1976 Stockford ................. B04C 5/04
   55/458
4,519,822 A * 5/1985 Hatano ................... B04C 5/081
   55/459.1
(Continued)

FOREIGN PATENT DOCUMENTS

CN   102652256 A   8/2012
EP      0128113 A  12/1984
(Continued)

OTHER PUBLICATIONS

Office Action dated Nov. 10, 2016, issued for Japanese Patent Application No. 2013-074767, 3 pgs.
(Continued)

*Primary Examiner* — Tony G Soohoo
*Assistant Examiner* — Elizabeth Insler
(74) *Attorney, Agent, or Firm* — Brooks Kushman P.C.

(57) ABSTRACT

The present invention is intended to reduce noise or vibration occurring in an exhaust gas mixer, and provided with: a mixer main body that has a hollow part extending in an axial direction; an inner pipe part that is provided in the hollow part along the axial direction; a gas introduction part that is provided to the mixer main body, and introduces mixing target gas into a space to spiral the mixing target gas; and a gas lead-out part that is provided in the inner pipe part to lead out the mixing target gas, wherein a central axis of the inner pipe part and a central axis of the hollow part are provided in mutually different positions.

6 Claims, 8 Drawing Sheets (51) Int. Cl.
*G01N 1/22* (2006.01)
*G01N 15/06* (2006.01)

(58) Field of Classification Search
CPC ......... B04C 5/103; F01N 1/085; F01N 1/086; F01N 1/087; F01N 1/088; F01N 1/12; F01N 1/14; F01N 13/007; F01N 13/082; F01N 13/12; F01N 2270/06; F01N 2270/10; B01J 19/2405
USPC ............ 366/165.1, 165.2; 181/228; 55/459.1
See application file for complete search history.

(56) References Cited

U.S. PATENT DOCUMENTS

| | | | | |
|---|---|---|---|---|
| 5,302,301 | A * | 4/1994 | Stamp | B01D 50/002 210/348 |
| 5,502,984 | A * | 4/1996 | Boehde | B01D 45/12 210/512.1 |
| 2006/0037294 | A1* | 2/2006 | Oh | A47L 9/1658 55/459.1 |
| 2011/0120096 | A1 | 5/2011 | Nakamura | |
| 2011/0296808 | A1 | 12/2011 | Brock et al. | |
| 2012/0036836 | A1 | 2/2012 | Dickow | |
| 2012/0266687 | A1 | 10/2012 | Takahashi | |

FOREIGN PATENT DOCUMENTS

| | | |
|---|---|---|
| EP | 1176293 A2 | 12/1984 |
| JP | 01-22024 B | 4/1989 |
| JP | 06-341950 | 12/1994 |
| JP | 10111222 A | 4/1998 |
| JP | 2011-106999 A | 6/2011 |
| JP | 2012-522229 A | 9/2012 |
| JP | 2013-532551 A | 8/2013 |
| JP | 5269794 B | 8/2013 |
| WO | 2012-015710 A1 | 2/2012 |

OTHER PUBLICATIONS

Office Action dated May 9, 2017 issued for Chinese patent application No. 201410098084.7, 12 pgs.

* cited by examiner

EXHAUST GAS MIXER AND CONSTANT VOLUME SAMPLING APPARATUS

CROSS-REFERENCE TO RELATED APPLICATION

This application claims priority to JP Application No. 2013-074767, filed Mar. 29, 2013, the disclosure of which is incorporated in its entirety by reference herein.

TECHNICAL FIELD

The present invention relates to an exhaust gas mixer that mixes mixing target gas containing exhaust gas, such as diluted exhaust gas produced by diluting exhaust gas with diluent gas, and to a constant volume sampling apparatus using the exhaust gas mixer.

BACKGROUND ART

In the past, as a dilution sampling system that dilutes collected exhaust gas with diluent gas such as air to measure the concentration of a component contained in the diluted exhaust gas, a constant volume dilution sampling apparatus (CVS) has been widely used.

In this CVS, as disclosed in JP 06-341950, on an upstream side of a flow rate control part including a critical flow venturi and a suction pump, an exhaust gas mixer for uniformly stirring/mixing exhaust gas and diluent gas is provided.

Also, the conventional exhaust gas mixer is a mixer of a cyclone system, and provided with: a mixer main body that has inside a hollow part extending in a predetermined axial direction; a gas introduction pipe that is connected to a side wall of the mixer main body to introduce the exhaust gas and the diluent gas into the hollow part; and a mixed gas lead-out pipe that is inserted into the mixer main body and provided with a central axis coaxially with the central axis of the hollow part.

However, in the exhaust gas mixer having the above-described configuration, the central axis of the mixed gas lead-out pipe and the central axis of the hollow part are provided coaxially with each other, so that a space between the mixer main body and the mixed gas lead-out pipe has a constant cross-sectional area in a spiral direction, and therefore a spiral velocity of the gases introduced from the exhaust gas introduction pipe is excessively increased to cause noise or vibration. Note that it is generally said that noise is proportional to the sixth to eighth power of a flow velocity. Also, there is a problem that the increase in gas spiral velocity causes resonance in the exhaust gas mixer to make the noise or vibration larger.

In addition, it is possible to decrease the flow velocity of the mixed gas flowing into the exhaust gas mixer; however, in the exhaust gas mixer used for the CVS, a flow rate is controlled so as to meet a constant flow rate through the critical flow venturi, and therefore the flow velocity of the mixed gas from the gas introduction part cannot be decreased.

SUMMARY OF INVENTION

Technical Problem

Therefore, the present invention is mainly intended to reduce vibration or noise that occurs due to a flow of mixing target gas containing exhaust gas in an exhaust gas mixer.

Solution to Problem

That is, the exhaust gas mixer according to the present invention is an exhaust gas mixer that mixes mixing target gas containing exhaust gas, and provided with: a mixer main body that has inside a hollow part extending in a predetermined axial direction; an inner pipe part that is provided in the hollow part along the axial direction; a gas introduction part that is provided to the mixer main body to introduce the mixing target gas into a space between the mixer main body and the inner pipe part; and a gas lead-out part that is provided in the inner pipe part to lead out the mixing target gas that has spiraled in the space, wherein a central axis of the inner pipe part and a central axis of the hollow part are provided in mutually different positions.

If so, the central axis of the inner pipe part and the central axis of the hollow part are provided in the mutually different positions, so that in the space between the mixer main body and the inner pipe part, a wide part and a narrow part are formed, and therefore the mixing target gas introduced through the gas introduction part alternately repeats having a fast flow velocity and a slow flow velocity in the process of spiraling in the space. This makes it possible to disturb a spiral velocity component in the process where the mixing target gas spirals, and therefore a spiral flow velocity of the mixing target gas can be slowed as a whole to reduce noise or vibration. Also, by slowing the spiral flow velocity of the mixing target gas as a whole, resonance can be made less likely to occur in the exhaust gas mixer, and this can also contribute to the reduction in noise or vibration.

Desirably, the gas introduction part is provided through a lateral circumferential wall of the mixer main body; and the central axis of the inner pipe part is provided with, as viewed from a central axis direction of the hollow part, in a direction along a tangent of the mixer main body at an inner end part of a connecting part between the mixer main body and the gas introduction part, being displaced toward a side opposite to an outer end part of the connecting part rather than the inner end part.

This makes it possible to easily spiral the exhaust gas introduced through the gas introduction part immediately after the introduction, and disturb the spiral velocity component in the process of spiraling.

In addition, in the case where the central axis of the inner pipe part is displaced toward the outer end part side rather than the inner end part side in the direction along the tangent of the mixer main body at the inner end part, the exhaust gas introduced through the gas introduction part hits against an outer circumferential surface of the inner pipe part to make it difficult to spiral, and therefore uniformity in mixing of the mixing target gas is reduced.

Desirably, the gas introduction part is provided along a tangent of an inner circumferential surface of the mixer main body to introduce the mixing target gas into the space along the inner circumferential surface.

If so, the mixing target gas introduced through the gas introduction part starts to flow along the inner circumferential surface of the mixer main body immediately after the introduction, and therefore the mixing target gas can be made more likely to be spiraled.

Desirably, the gas introduction part is provided with a guide plate that guides the exhaust gas introduced through the gas introduction part so as to move toward an inner circumferential surface of the mixer main body.

If so, the mixing target gas introduced through the gas introduction part hits against the guide plate to move toward the inner circumferential surface of the mixer main body, and therefore the mixing target gas can be made likely to be spiraled.

In the case where the mixing target gas introduced through the gas introduction part hits against the outer circumferential surface of the inner pipe part, in addition to a flow in a spiral direction, mixing target gas flowing in a direction different from the spiral direction is produced. If so, a spiral component is canceled out, which becomes a factor damaging the uniformity in mixing of the mixing target gas.

For this reason, desirably, as viewed forward from the gas introduction part, the guide plate is provided so as to hide the inner pipe part.

If so, the mixing target gas introduced through the gas introduction part does not directly hit against the outer circumferential surface of the inner pipe part, and therefore it is possible to surely and easily spiral the mixing target gas.

Advantageous Effects of Invention

According to the present invention configured as described, the central axis of the inner pipe part and the central axis of the hollow part are provided in the mutually different positions, and therefore vibration or noise occurring due to a flow of the mixing target gas containing the exhaust gas in the exhaust gas mixer can be reduced.

DESCRIPTION OF EMBODIMENTS

In the following, an exhaust gas sampling apparatus using an exhaust gas mixer according to the present invention is described with reference to the drawings.

An exhaust gas sampling apparatus 100 of the present embodiment is one that is used for a gas analyzing system for analyzing a component contained in exhaust gas emitted from, for example, an engine or the like, and of a dilution sampling system that dilutes the exhaust gas with diluent gas such as air (diluent air) several times (e.g., 10 to 20 times) to perform concentration measurement.

Figure 1:
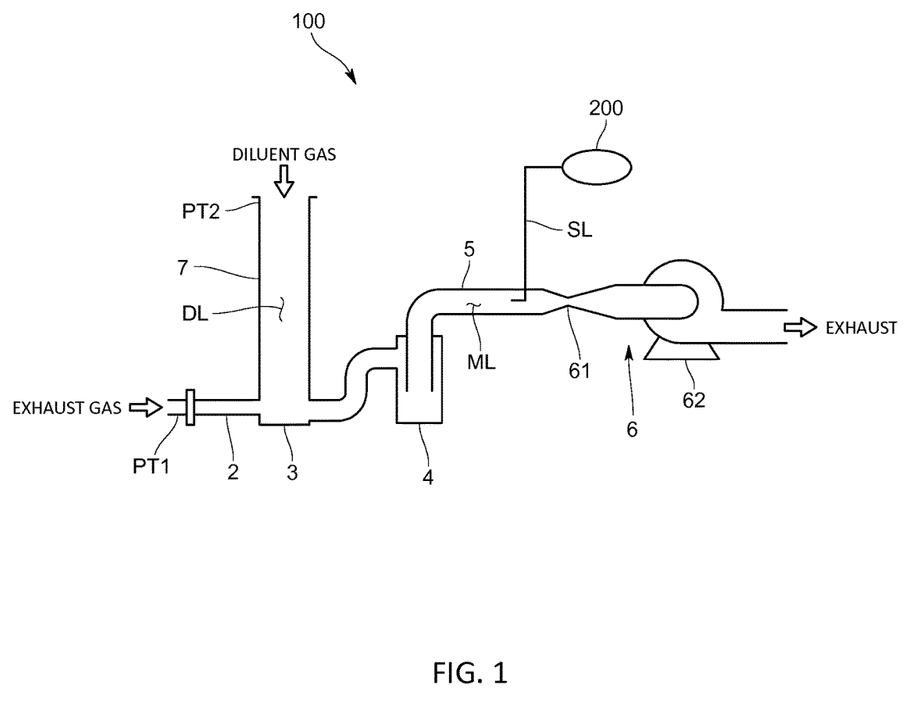
FIG. 1 is a diagram illustrating a configuration of an exhaust gas sampling apparatus of the present embodiment.
Figure 2:
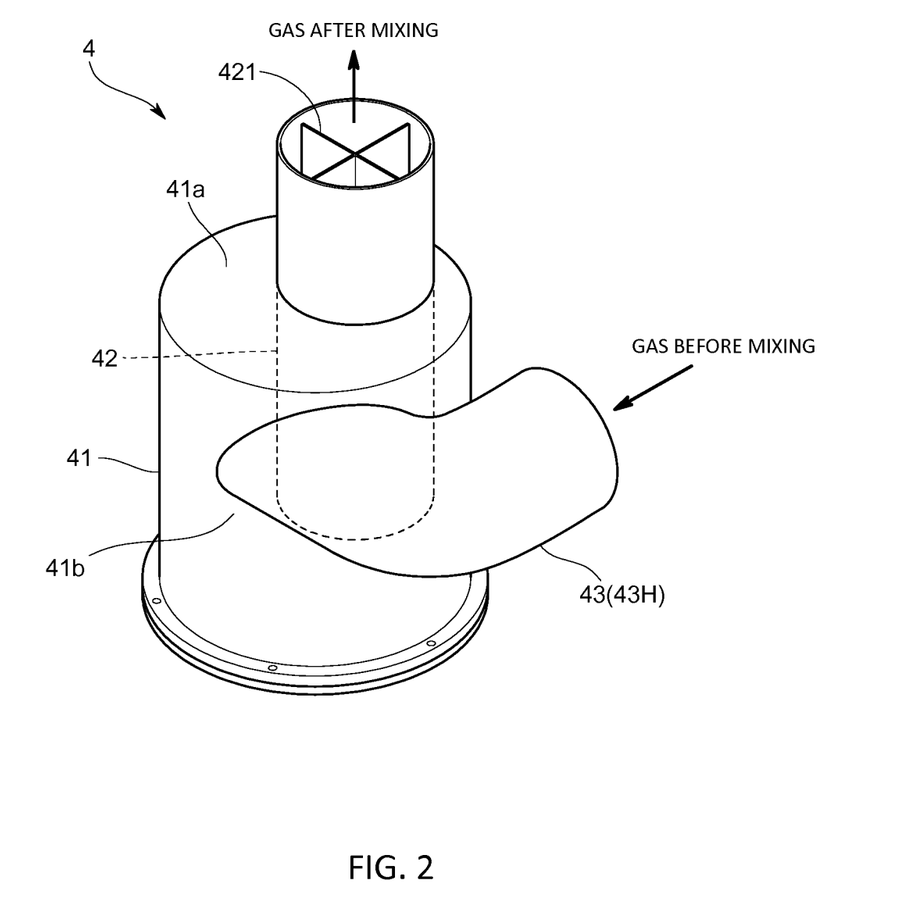
FIG. 2 is a perspective view illustrating a configuration of an exhaust gas mixer of the same embodiment.

Specifically, the exhaust gas sampling apparatus 100 is provided with a constant volume sampling part, and as illustrated in FIG. 1, provided with: a main flow path ML of which one end is connected to an exhaust gas introduction port PT1 for introducing the exhaust gas; and a diluent gas flow path DL of which one end is connected to a diluent gas introduction port PT2 for introducing the diluent gas and the other end is connected to the main flow path ML.

The main flow path ML is configured to include: an exhaust gas introduction pipe 2 of which one end is provided with the exhaust gas introduction port PT1 to introduce the exhaust gas; a mixing part 3 that is connected to the exhaust gas introduction pipe 2; an exhaust gas mixer 4 that is connected downstream of the mixing part 3 to uniformly stir and mix diluted exhaust gas (mixed gas); a sampling pipe 5 that is connected to the exhaust gas mixer 4, and intended to sample the mixed gas that is controlled to have a constant flow rate as will be described later; and a constant flow rate control device 6 that is connected to the sampling pipe 5. Also, the diluent gas flow path DL is configured to include a diluent gas introduction pipe 7 of which one end is provided with the diluent gas introduction port PT2. In addition, the diluent gas introduction port PT2 is provided with a filter (not illustrated) for removing impurities in the air.

The mixing part 3 is one that is connected with the diluent gas introduction pipe 7 constituting the diluent gas flow path DL and the exhaust gas introduction pipe 2, and referred to as, for example, a mixing tee. Also, the sampling pipe 5 for performing constant volume sampling of the mixed gas is connected with a sampling flow path SL for collecting and introducing diluted exhaust gas into an analyzing device 200 such as a gas collecting bag, PM collecting filter, or exhaust gas analyzing device.

The constant flow rate control device 6 is one that performs flow rate control so as to make a total flow rate of the exhaust gas introduced from the exhaust gas introduction pipe 2 and the diluent gas introduced from the diluent gas introduction pipe 7 constant, and configured to include: a main venturi 61 that includes a critical flow venturi (CFV) connected downstream of the sampling pipe 5; and a suction pump 62 that is connected downstream of the main venturi 61, such as a blower. The suction pump 62 makes a differential pressure between pressures on upstream and downstream sides of the main venturi 61 equal to or more than a predetermined value to thereby make the total flow rate constant. In addition, the diluted exhaust gas sucked by the suction pump 62 is discharged outside.

Further, the exhaust gas mixer 4 of the present embodiment is, as illustrated in FIGS. 2 to 5, provided with: a mixer main body 41 that has inside a hollow part 411 extending in a predetermined axial direction L; an inner pipe part 42 that is provided in the hollow part 411 along the axial direction L; a gas introduction part 43 that is provided to the mixer main body 41, and introduces the exhaust gas and the diluent gas integrally serving as mixing target gas into a space S between the mixer main body 41 and the inner pipe part 42 to spiral the mixing target gas; and a gas lead-out part 44 that is provided in the inner pipe part 42 and leads out the mixing target gas that has spiraled in the space S. Note that the mixing target gas in the present embodiment is the diluted exhaust gas (the exhaust gas diluted with the diluent gas) produced in the mixing part 3.

Figure 3:
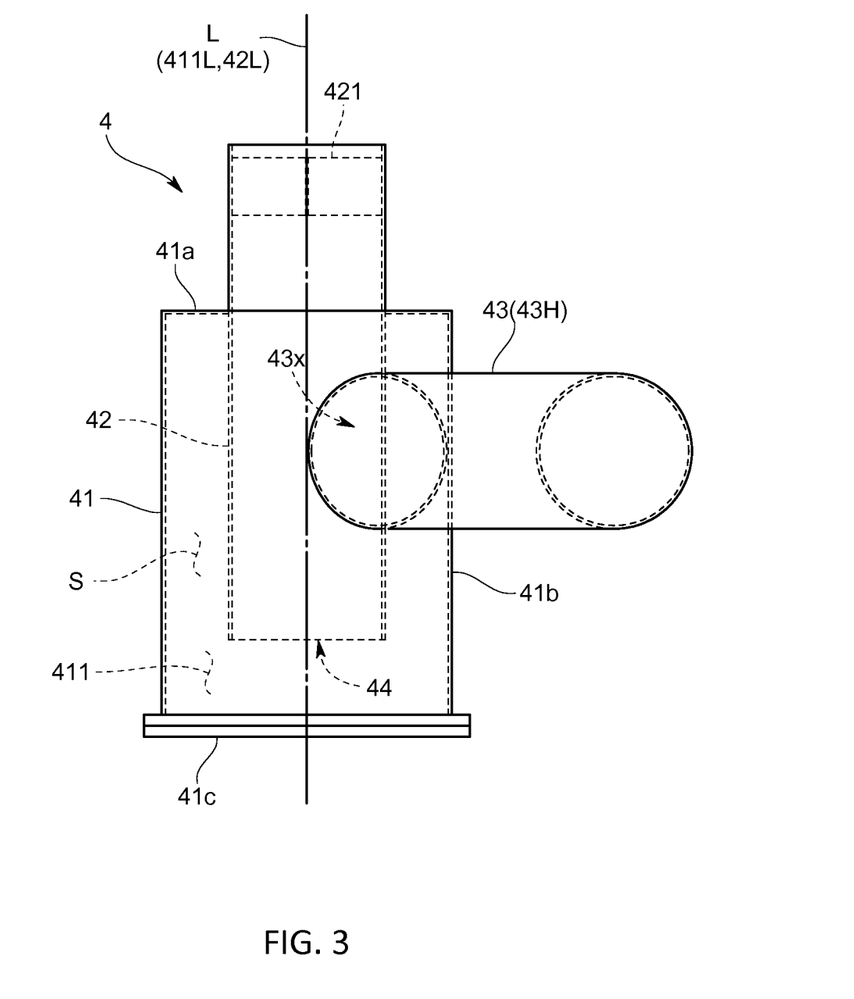
FIG. 3 is a side view illustrating the configuration of the exhaust gas mixer of the same embodiment.
Figure 4:
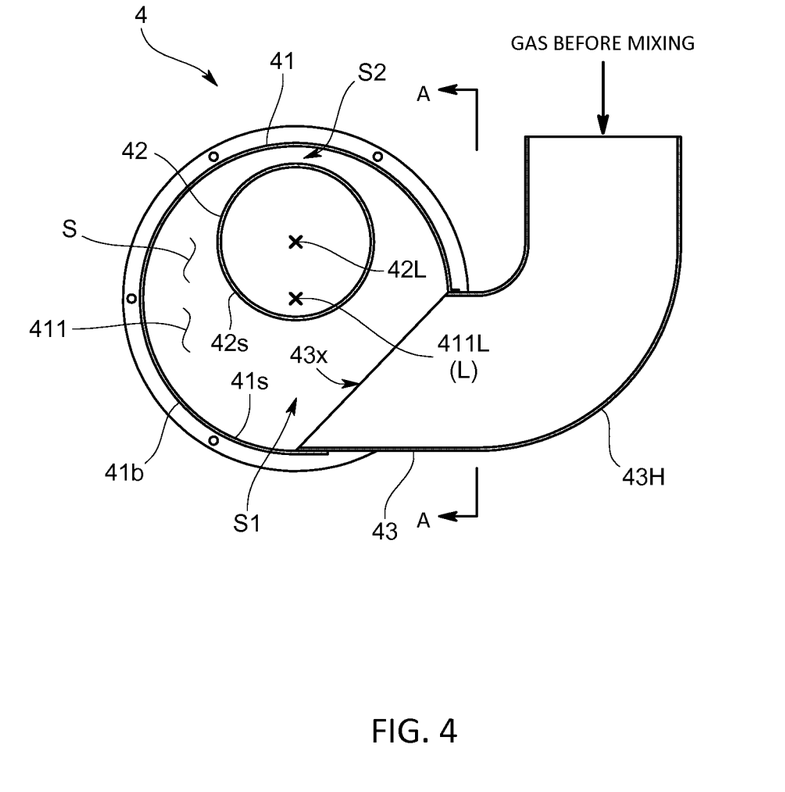
FIG. 4 is a transverse cross-sectional view illustrating the configuration of the exhaust gas mixer of the same embodiment.

As particularly illustrated in FIGS. 3 and 4, the mixer main body 41 has inside the hollow part 411 of a substantially columnar shape extending in the axial direction L. The mixer main body 41 in the present embodiment is one that is formed in a cylindrical shape having the hollow part 411, of which both end parts in the axial direction L are closed.

Figure 5:
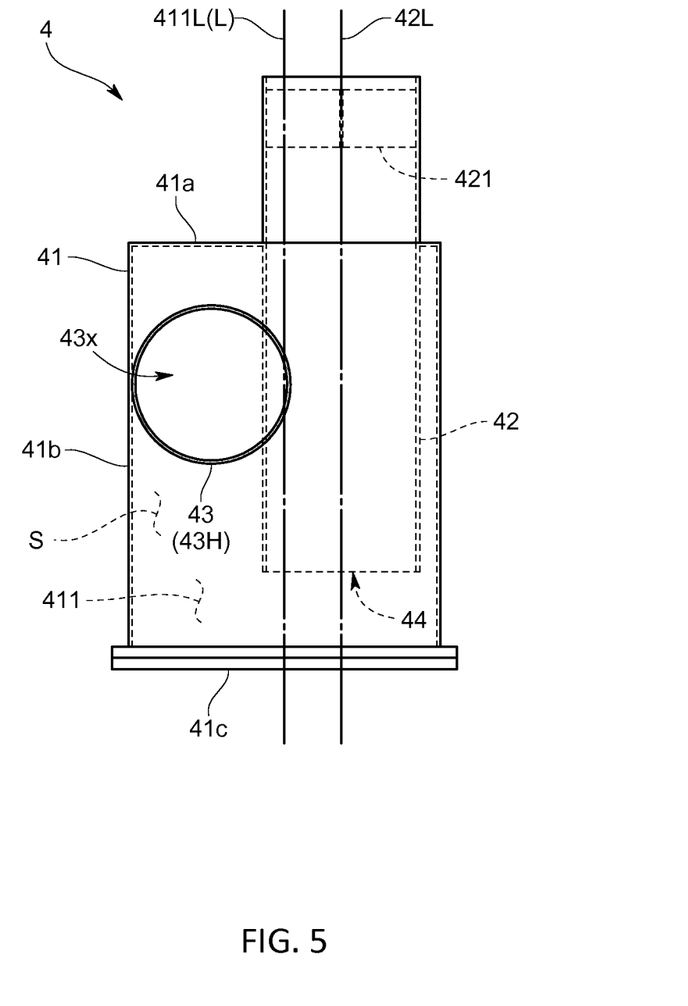
FIG. 5 is a schematic diagram illustrating a region where a central axis of an inner pipe part is provided.

The inner pipe part 42 is, as particularly illustrated in FIGS. 3 and 5, provided along the axial direction L with penetrating through one end wall 41a of the mixer main body 41, and a fore end part thereof is provided so as to be positioned inside the hollow part 411 of the mixer main body 41. The inner pipe part 42 is one that is formed in a circular pipe shape, and at least inside the hollow part 411, formed in a straight pipe shape.

As particularly illustrated in FIG. 4, the gas introduction part 43 is provided on the one end wall 41a side through a lateral circumferential wall 41b of the mixer main body 41. Also, the gas introduction part 43 is one that is provided so as to lie along a tangent of an inner circumferential surface 41s of the mixer main body 41, and introduces the mixing target gas into the spiral space S along the inner circumferential surface 41s. Specifically, through the lateral circumferential wall 41b of the mixer main body 41, the gas introduction part 43 is formed of a gas introduction pipe 43H extending in a direction orthogonal to the axial direction L. As described, the gas introduction part 43 has a gas introduction port 43x and the gas introduction pipe 43H. This enables a time and path for the mixing target gas introduced into the spiral space S to arrive at the gas lead-out part 44 to be increased to further mix the mixing target gas as compared with the case where the gas introduction pipe 43H is obliquely provided so as to face to the gas lead-out part 44. Note that the gas introduction pipe is connected to the mixing part 3. The gas introduction port 43x of the gas introduction part 43 is opened in a position deviated from the axial direction L.

The gas lead-out part 44 is, as particularly illustrated in FIGS. 3 and 5, formed in an insertion side fore end part of the inner pipe part 42, and specifically, formed as a fore end opening part of the inner pipe part 42. That is, the gas lead-out part 44 is opened with facing to the other end wall 41c side orthogonal to the axial direction L of the mixer main body 41. Also, the gas lead-out part 44 is positioned on the other end wall 41c side rather than the gas introduction part 43 side. The mixing target gas flowing into the gas lead-out part 44 passes through the inside of the inner pipe part 42, and flows to the sampling pipe 5 connected to the inner pipe part 42. In addition, inside the inner pipe part 42, straightening vanes 421 are provided along a flow path direction so as to, for example, divide a flow path inside the inner pipe part 42 into four flow paths, and configured to cancel a spiral flow of the diluted exhaust gas flowing from the inner pipe part 42 to the sampling pipe 5.

Further, in the exhaust gas mixer 4 of the present embodiment, as particularly illustrated in FIGS. 4 and 5, a central axis 42L of the inner pipe part 42 and a central axis 411L of the hollow part 411 are provided in mutually different positions. That is, the central axis 42L of the inner pipe part 42 is eccentric with respect to the central axis 411L of the hollow part 411. Specifically, the central axis 42L of the inner pipe part 42 and the central axis 411L of the hollow part 411 are provided in the mutually different positions, and also provided so as to make the axes 42L and 411L parallel to each other.

Figure 6:
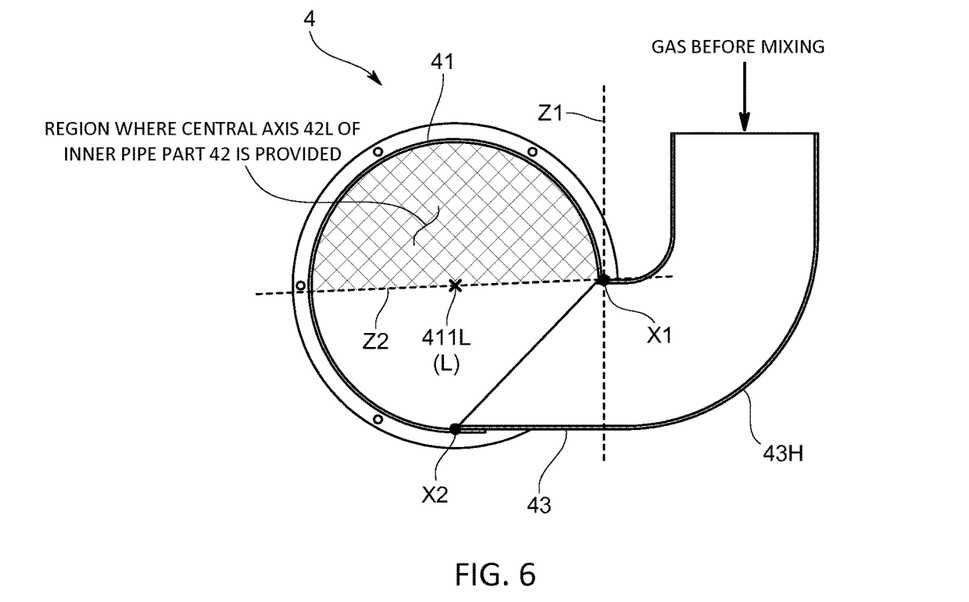
FIG. 6 is an A-A line cross-sectional view illustrating the configuration of the exhaust gas mixer of the same embodiment.

In detail, as illustrated in FIG. 6, the central axis 42L of the inner pipe part 42 is provided with, as viewed from a central axis direction of the hollow part 411, in a direction along a tangent Z1 of the mixer main body 41 at an inner end part X1 of a connecting part between the mixer main body 41 and the gas introduction part 43, being displaced toward a side opposite to an outer end part X2 of the connecting part rather than the inner end part X1. That is, the central axis 42L of the inner pipe part 42 is provided with being displaced so as to be included in a shaded area in FIG. 6. In addition, the inner end part X1 is a back side end part in a gas introduction direction of the gas introduced from the gas introduction part 43, and the outer end part X2 is a front side end part in the gas introduction direction. Further, in other words, the central axis 42L of the inner pipe part 42 is provided with being displaced toward the side opposite to the outer end part X2 with respect to a virtual straight line Z2 that connects the inner end part X1 and the center (central axis 411L) of the hollow part 411 to each other.

In the present embodiment, as illustrated in FIGS. 4 and 6, the exhaust gas introduction part 43 is provided on the right side of a lower part of the mixer main body 41, and therefore the central axis 42L of the inner pipe part 42 is provided with being displaced upward eccentrically with respect to the central axis 411L of the hollow part 411. In the present embodiment, the central axis 42L of the inner pipe part 42 is provided with being displaced in a direction away from the gas introduction part 43 with respect to the central axis 411L of the hollow part 411.

In the exhaust gas mixer 4, the central axis 42L of the inner pipe part 42 and the central axis 411L of the hollow part 411 are provided in the mutually different positions, and therefore as illustrated in FIG. 4, in the space S between the mixer main body 41 and the inner pipe part 42, a wide part S1 and a narrow part S2 are formed. In addition, the wide part S1 is a part having a large distance between the inner circumferential surface 41s of the mixer main body 41 and an outer circumferential part 42s of the inner pipe part 42, and the narrow part S2 is a part having a small distance between the inner circumferential surface 41s of the mixer main body 41 and the outer circumferential surface 42s of the inner pipe part 42. Also, the gas introduction port 43x of the gas introduction part 43 is provided so as to face to the wide part S1 in the space S. That is, in a region immediately after the gas introduction through the gas introduction part 43, a distance between the inner circumferential surface 41s of the mixer main body 41 and the outer circumferential surface 42s of the inner pipe part 42 is increased as compared with the case of arranging the mixer main body 41 and the inner pipe part 42 concentrically with each other. In addition, the mixing target gas introduced into the space S through the gas introduction part 43 forms the spiral flow that passes through the wide part S1 of the space S and flows toward the narrow part S2. Further, the mixing target gas having passed through the narrow part S2 again flows toward the wide part S1. While repeating this, the mixing target gas flows toward the fore end part of the inner pipe part 42 with spiraling, then from the gas lead-out part 44 in the fore end part of the inner pipe part 42, passes through the inside of the inner pipe part 42, and is led outside the exhaust gas mixer 4.

According to the exhaust gas sampling apparatus 100 according to the present embodiment configured as described, the central axis 42L of the inner pipe part 42 and the central axis 411L of the hollow part 411 are provided in the mutually different positions, so that the wide part S1 and the narrow part S2 are formed in the space S between the mixer main body 41 and the inner pipe part 42 (see FIG. 4), and therefore the mixing target gas introduced through the gas introduction part 43 alternately repeats having a fast flow velocity and a slow flow velocity in the process of spiraling in the space S. This makes it possible to disturb a spiral velocity component in the process where the mixing target gas spirals, and therefore a spiral flow velocity of the mixing target gas can be slowed as a whole to reduce noise or vibration. Also, by slowing the spiral flow velocity of the mixing target gas as a whole, resonance can be made less likely to occur in the exhaust gas mixer 4, and this can also contribute to the reduction in noise or vibration.

Note that the present invention is not limited to the above-described embodiment.

For example, the displacement direction of the central axis 42L of the inner pipe part 42 with respect to the central axis 411L of the hollow part 411 is not limited to that in the above-described embodiment, and the central axis 42L may be displaced in any circumferential direction. Also, the above-described embodiment is configured to make the central axis 411L of the hollow part 411 and the central axis 42L of the inner pipe part 42 parallel to each other; however, the present invention may be adapted to provide the central axis 42L of the inner pipe part 42 obliquely to the central axis 411L of the hollow part 411.

In the above-described embodiment, described is the case where the central axis 42L of the inner pipe part 42 is displaced toward the side opposite to the outer end part X2 rather than the inner end part X1 in the direction along the tangent Z1; however, the central axis 42L may be displaced toward the outer end part X2 side rather than the inner end part X1 side in the direction along the tangent Z1. In addition, in this case, although the mixing target gas introduced through the gas introduction part 43 is made less likely to spiral, an effect of slowing down the spiral velocity can be produced.

Also, in the above-described embodiment, in the region immediately after the gas introduction through the gas introduction part 43, the distance between the inner circumferential surface 41s of the mixer main body 41 and the outer circumferential surface 42s of the inner pipe part 42 may be configured to be larger than a pipe diameter of the gas introduction pipe 43H. This configuration makes it possible to easily spiral the exhaust gas introduced through the gas introduction part 43 immediately after the introduction, and disturb the spiral velocity component in the process of spiraling.

Figure 7:
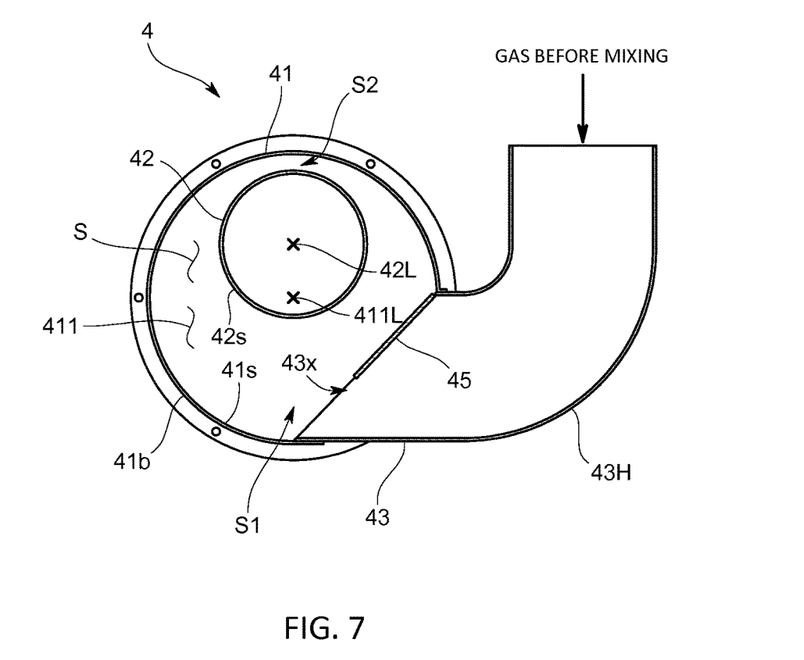
FIG. 7 is a transverse cross-sectional view illustrating a configuration of an exhaust gas mixer in a variation.
Figure 8:
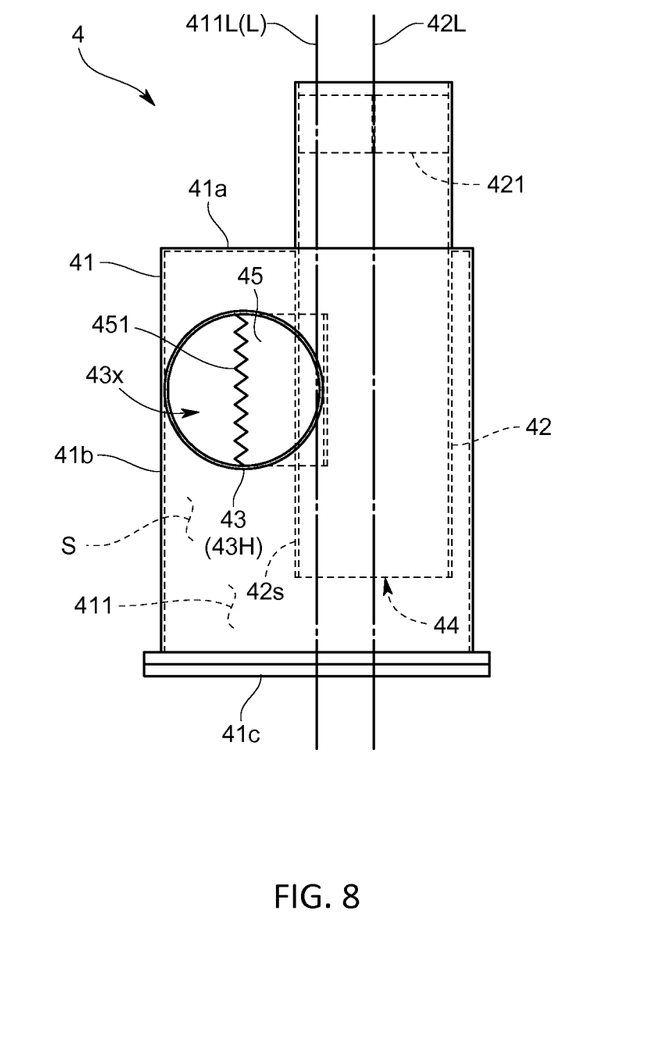
FIG. 8 is an A-A line cross-sectional view of the exhaust gas mixer in the variation.

Further, in addition to the configuration of the exhaust gas mixer 4 of the above-described embodiment, as illustrated in FIGS. 7 and 8, a front part of the gas introduction part 43 may be provided with a guide plate 45 that guides the exhaust gas introduced through the gas introduction part 43 so as to move toward the inner circumferential surface 41s of the mixer main body 41. The guide plate 45 is provided with tilting toward the inner circumferential 41s side of the mixer main body 41 with respect to the flow direction of the mixing target gas introduced through the gas introduction part 43. This can make the mixing target gas more likely to be spiraled because the mixing target gas introduced through the gas introduction part 43 hits against the guide plate 45 and moves toward the inner circumferential surface 41s of the mixer main body 41.

Further, in the case of providing the guide plate 45, as illustrated in FIG. 8, the inner pipe part 42 may be adapted to be hidden by the guide plate 45 as viewed forward from the gas introduction part 43. This makes it possible to suppress the production of mixing target gas flowing in a direction different from the spiral direction because the mixing target gas introduced through the gas introduction part 43 does not directly hit against the outer circumferential surface 42s of the inner pipe part 42. Accordingly, it is possible to surely and easily spiral the mixing target gas introduced through the gas introduction part 43.

Still further, as illustrated in FIG. 8, a downstream side end part 451 of the guide plate 45 may be one that has an uneven shape such as a saw-toothed shape in a plan view by providing, for example, a plurality of triangular protrusions. This makes the mixing target gas passing through the guide plate 45 swirl to produce various components, and the components are cancelled out, so that the spiral flow velocity of the mixing target gas is slowed, and therefore noise can be reduced.

Figure 9:
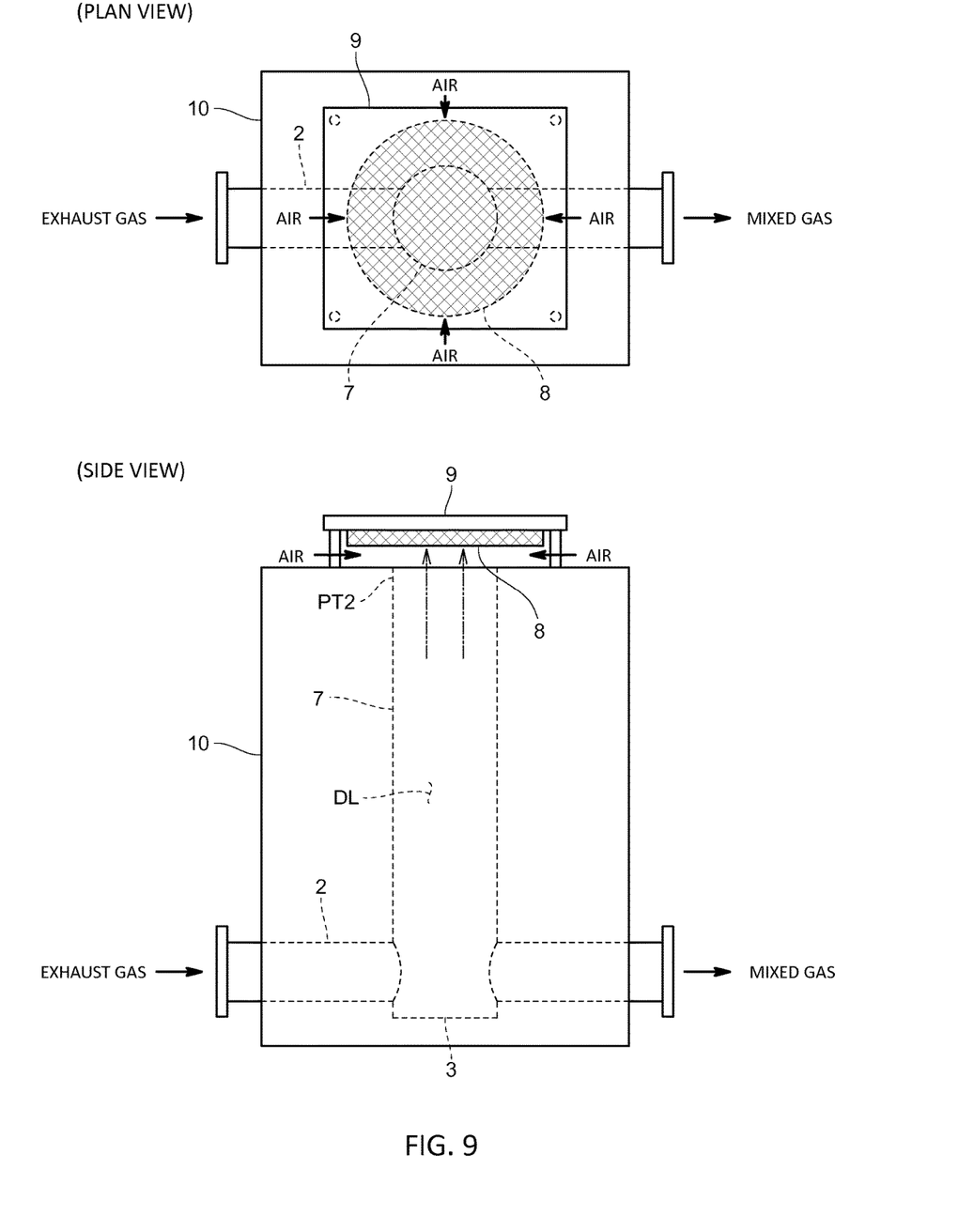
FIG. 9 is a schematic diagram illustrating a sound absorbing structure in another variation.

In addition, in order to improve noise reduction performance as the exhaust gas sampling apparatus, as illustrated in FIG. 9, a sound absorbing member 8 can be probably provided so as to face to an opening of the diluent gas introduction port PT2 and surround the whole of the opening of the diluent gas introduction port PT2. Note that the sound absorbing member 8 is provided with being separated upward from the opening of the diluent gas introduction port PT2 so as to enable the air to be introduced into the diluent gas introduction port PT2. In addition, the sound absorbing member 8 is fixed by a fixing member 9 to a housing 10 that contains the diluent gas introduction pipe 7 constituting the diluent gas flow path DL and the mixing part 3.

Still in addition, the exhaust gas sampling apparatus of the above-described embodiment is one that dilutes a total amount of the exhaust gas; however, the exhaust gas sampling apparatus may be one that partially dilutes the exhaust gas. That is, the exhaust gas sampling apparatus may be one adapted such that the exhaust gas introduction port PT1 collects part of the exhaust gas to introduce the part into the main flow path ML.

Still further, the constant flow rate control device 6 in the above-described embodiment is one using the critical flow venturi; however, the constant flow rate control device 6 may be one using, in addition to the critical flow venturi, a critical flow orifice (CFO). Alternatively, the constant flow rate control device 6 may be one that is of a constant volume pump system not using the critical flow venturi.

Besides, it should be appreciated that the present invention is not limited to any of the above-described embodiments, but can be variously modified without departing from the scope thereof.

REFERENCE SIGNS LIST

100: Exhaust gas sampling apparatus (constant volume sampling apparatus)
4: Exhaust gas mixer
41: Mixer main body
41s: Inner circumferential surface of mixer main body
L: Predetermined axial direction
411: Hollow part
411L: Central axis of hollow part
42: Inner pipe part
42L: Central axis of inner pipe part
S: Space between mixer main body and inner pipe part
43: Gas introduction part
44: Gas lead-out part
45: Guide plate

What is claimed is:
1. An exhaust gas mixer that mixes target gas containing exhaust gas and diluent gas to form diluted exhaust gas, the exhaust gas mixer comprising:
a mixer main body having an inner circumferential surface defining a hollow part extending in an axial direction, and configured to mix target gas containing exhaust gas and diluent gas;
an inner pipe part disposed in the hollow part along the axial direction, and passing through and projecting away from a closed end of the mixer main body, wherein a central axis of the inner pipe part and a central axis of the hollow part are disposed in different positions;
a gas introduction part configured to introduce the target gas into a space between the mixer main body and the inner pipe part;
a guide plate disposed within the hollow part at an inner end part of a connecting part between the mixer main body and the gas introduction part, tilted toward an outer end part of the connecting part, and configured to guide the target gas exiting the gas introduction part toward the outer end part at the inner circumferential surface to promote spiraling of the target gas in the space; and
a gas lead-out part disposed in the inner pipe part to lead out the diluted exhaust gas that has been mixed by the spiraling.

2. The exhaust gas mixer according to claim 1, wherein:
the gas introduction part passes through a lateral circumferential wail of the mixer main body; and
the central axis of the inner pipe part is displaced toward a side opposite to the outer end part rather than the inner end part.

3. The exhaust gas mixer according to claim 1, wherein the gas introduction part is disposed along a tangent of an inner circumferential surface of the mixer main body to introduce the mixing target gas into the space along the inner circumferential surface.

4. The exhaust gas mixer according to claim 1, wherein as viewed forward from the gas introduction part, the guide plate is arranged so as to hide the inner pipe part.

5. A constant volume sampling apparatus comprising
a constant volume sampling part that samples mixed gas that is controlled to have a constant flow rate, wherein
the constant volume sampling part comprises:
a main flow path through which exhaust gas flows;
a diluent gas flow path through which diluent gas flows, the diluent gas flow path being connected to the main flow path;
an exhaust gas mixer that is provided in the main flow path to mix the exhaust gas and the diluent gas;
a constant flow rate control device that is provided downstream of the exhaust gas mixer in the main flow path to control mixed gas that is a mixture produced by the exhaust gas mixer, the mixed gas being controlled to have a constant flow rate; and
a sampling flow path that is connected between the exhaust gas mixer and the constant flow rate control device in the main flow path to sample the mixed gas that is controlled to have the constant flow rate, wherein
the exhaust gas mixer comprises the exhaust gas mixer according to claim 1.

6. The exhaust gas mixer according to claim 1, wherein the inner pipe part includes straightening vanes along a flow path direction configured to cancel a spiral flow of the diluted exhaust gas flowing through the inner pipe part.

* * * * *